United States Patent
Bruss et al.

(10) Patent No.: US 6,537,658 B1
(45) Date of Patent: Mar. 25, 2003

(54) FILM-BASED DRESSING MATERIAL WITH IMPRINT

(75) Inventors: Witta Bruss, München (DE); Sebastian Trotter, Buchholz (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/684,445

(22) Filed: Oct. 6, 2000

(30) Foreign Application Priority Data

Oct. 19, 1999 (DE) .......................... 198 50 295

(51) Int. Cl.⁷ .............................. B32B 15/04
(52) U.S. Cl. .................. 428/354; 428/355; 428/908; 156/277; 156/244.16
(58) Field of Search ................... 428/355, 345, 428/354, 908, 196; 424/423, 449, 448; 156/277, 244.15, 244.16

(56) References Cited

U.S. PATENT DOCUMENTS

| 5,099,832 A | * | 3/1992 | Ward .......................... 602/57 |
| 5,437,621 A | * | 8/1995 | Andrews et al. .............. 602/42 |
| 5,783,209 A | * | 7/1998 | Imamura et al. ............ 424/448 |
| 6,210,704 B1 | * | 4/2001 | Sasaki et al. ............... 424/443 |

* cited by examiner

*Primary Examiner*—Merrick Dixon
(74) *Attorney, Agent, or Firm*—Norris McLaughlin & Marcus

(57) ABSTRACT

Film-based dressing material lined on the side remote from the wound with a backing material of the same size as the film, which in particular is transparent, the wound-facing side of the film bearing an imprint.

8 Claims, 1 Drawing Sheet

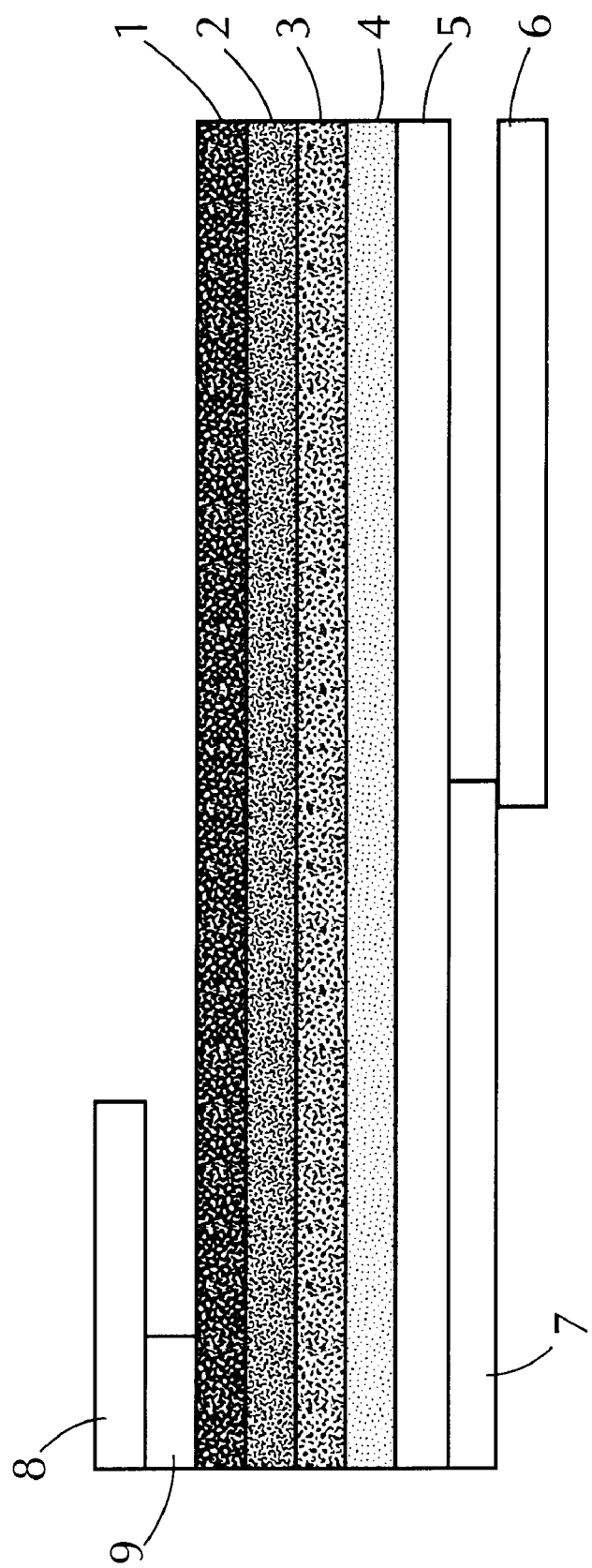

FILM-BASED DRESSING MATERIAL WITH IMPRINT

The invention relates to a film-based dressing material with imprint and a process for producing the printed dressing material.

Film-based dressing materials are known. In particular, the films comprise polyurethane. These PU films are used, inter alia, as backing materials for plasters for covering wounds.

The PU film plasters are produced by spreading a PU dispersion (preferably Impranil® from Bayer AG) two-dimensionally on an appropriate auxiliary backing, preferably a surface-embossed PE film, and drying the dispersion to form a film. Coating and drying may be carried out a number of times, producing a layered structure in which the layers are visually indistinguishable and inseparable.

The resulting auxiliary backing/PU film(s) assembly may be coated on the other side from the auxiliary backing with a suitable adhesive composition and lined with release paper, cut to form the stock roll, and processed to individual plasters by applying a wound cover paper and enclosing paper. The plaster produced in the manner set out above is transparent to opaque, depending on the coat thickness and the adhesive composition selected, with the centrally applied wound pad showing below the backing film.

At the time of application of the plasters, the stabilizing PE auxiliary backing is delaminated in order to make use of the flexible properties of the PU film.

Such plasters are comprehensively described in the prior art.

DE 40 26 755 A1 discloses a film-based dressing material lined on one side with a backing material which possesses the same size as the film and has at least one grip strip, and is provided on the other side with a self-adhesive layer. The grip strips for removing the backing material are arranged within its peripheral extent. Preferably, only one grip strip is applied on the backing material. DE 43 14 834 C2 discloses a film-based dressing material lined on one side with a backing material which possesses the same size as the film and has at least one grip strip, and is provided on the other side with a self-adhesive layer. The grip strips for removing the backing material are arranged within its peripheral extent. Preferably, only one grip strip is applied on the backing material.

It is advantageous to print the backing materials of plasters, for example for adolescents and children, for whom the application of plasters is fairly unpopular. This is because plasters are associated with negative recollections such as of pain, possibly bleeding or injuries. In order to raise the visual stimulus for children and adolescents, the imprints may be provided in particular with at least one cartoon figure. The printed film plasters encountered on the market consist primarily of PVC, PE, PET and other oligomeric backing films, which are usually relatively thick, relatively inflexible, relatively unconforming, relatively hard, and impermeable to water vapour in comparison to the PU films described, inter alia, in DE 40 26 755 A1 and DE 43 14 834 C2.

DE U 74 20 413 describes a badge which on its visible surface has a two-dimensional or three-dimensional reproduction of at least one figured representation which is familiar to and preferably popular with children, the said badge being characterized in that it is designed as a wound plaster having a cover layer which is made of material which is gentle on wounds and/or promotes healing and/or breathes, which forms the backing material for the figured representation, and which has regions that can be adhered to the skin. This badge too has regularly shaped backings onto which the desired figured representation is printed.

In general, however, plasters have predominantly no imprint on the side of the plaster backing material opposite from the body.

Only quite recently have plasters of this kind been encountered on the market. For instance, so-called Junior-Strips® bearing an imprint consisting in particular of representations of drawn figures, on a plaster of conventional form, which enjoys very great popularity especially among children, are marketed.

DE 197 09 606 A1, furthermore, describes a plaster for adhesive bonding to the skin, in particular for the covering of relatively small wounds, comprising a backing material which is provided on its bottom side with a dermatologically compatible self-adhesive layer. Some or all of the top side of the backing material—preferably a polyethylene film—bears a long-afterglow imprint formed by a coating system into which a long-afterglow pigment has been incorporated. Also described is a process for producing a plaster of this kind, which comprises the following steps:

a) at least one printing of the top side of the backing material over its full area with white flexographic printing ink by flexographic or screen printing,
 b) if desired, printing of the part-areas of the top side of the backing material that are not to be printed in step d) by flexographic printing,
 c) preparation of the mixture comprising a coating system and the afterglow pigment,
 d) printing of the top side of the backing material with the mixture, preferably by screen printing, in the case of partial printing, using a screen mechanism to fill in the white areas defined in step b), and
 e) if desired, postcrosslinking of the mixture by means of UV radiation or thermally.

It is an object of the invention to provide a film-based dressing material which bears an impression, especially one applied by reversal printing.

This object is achieved by means of a film-based dressing material as specified in the main claim. The subsidiary claims relate to advantageous developments of the dressing material and to a process for producing the dressing material of the invention.

The invention accordingly provides a film-based dressing material lined on the side remote from the wound with a backing material of the same size as the film, which in particular is transparent, the wound-facing side of the transparent film bearing an imprint. This imprint is applied in particular by reversal printing. In a reversal printing process, a mirror-inverted print is used. When the impression/inscription is viewed from the side remote from the wound, through the film, it is perceived in normal form.

By means of the impression it is possible, for example, to apply patterns, or the impression may be made over the entire area, so that the colour of the backing is adapted to the skin and thus the product can be made less conspicuous. Particular mention should be made in this context of the economic and cost advantages relative to a process of colouring whatever kinds of backing materials. Furthermore, there is great flexibility in the selection of the inks at a cost which is constant and independent of volume.

A further advantage consists in the optical lamination (by printing at the corresponding wound pad position of the backing material) of the wound backing, which in the case of very severe bleeding of the wound becomes soaked through and is perceived visually from the outside as disruptive.

In a first preferred embodiment of the dressing material, at least one further film is present on the transparent film with the imprint, and thus covers the imprint. As a result, the printing ink is protected between the films and has no direct contact with the adhesive composition which may be applied subsequently, or its auxiliaries. It is of advantage in this context that the use of any printing ink or coating, examples being UV printing inks, thermal printing inks, particular microcapsule coatings, etc., is made possible. This protective covering of the impression excludes interactions which might take place between the printed PU film side with the solvent-based adhesive compositions, the UV adhesive compositions, the dispersion adhesive compositions and/or the thermoplastic adhesive compositions such as hot-melts. Interactions between the adhesive compositions and any solvents, pigments, binders or additives that may be present in the printing ink are likewise unable to occur. In particular, within the storage life of years that is expected of plasters, any adverse influence on print quality or adhesion properties is suppressed.

Preference is further given to a dressing material wherein the wound-facing side is provided with a self-adhesive layer on which a wound pad may be arranged. The adhesive layer on the film preferably has, for example, a bond strength on steel of from about 2 to 4 N/cm, it being necessary to reinforce the test material on its reverse side with a non-elastic adhesive film, since the aforementioned film is highly extensible. The measurement itself takes place in accordance with DAB [German Pharmacopoeia] 9.

On its preferably self-adhesively treated side, which later is the side that faces the skin, the dressing material of the invention is lined over its whole width, up until the time of use, usually with an anti-adhesive backing material, such as siliconized paper. This material protects the self-adhesive layer comprising an adhesive composition which possesses good dermatological compatibility and is based, for example, on acrylates, preferably applied by the transfer process, and also stabilizes the product as a whole. In a conventional manner, the liner may be designed as a single piece or, preferably, in two parts.

The dressing material may be used as it is; alternatively, a customary absorbent wound pad smaller than the adhesive area may additionally be applied centrally in an appropriate width, so that the material may be used directly as a wound dressing. A dressing of this kind with all-round adhesive bonding is particularly advantageous since it is impervious to germs and is water-resistant.

The film itself preferably comprises elastic, thermoplastic polyurethanes, as described in DE 19 34 710 C, which are notable for good dermatological compatibility and also oxygen and water-vapour permeability. Aliphatic polyester urethanes have proven to be particularly advantageous.

A preferred film is from 30 to 40 $\mu$m thick, transparent, has an elongation at break of more than 450%, and has a water vapour permeability of more than 500 g/m$^2$ in 24 h at 38° C. and 95% relative humidity in accordance with DAB.

In addition, however, it is also possible to use films on a different basis, such as, for example, acrylate copolymers or the other known film-forming elastic polymers. The thickness of the films may be from 15 to 300 $\mu$m, preferably from 15 to 80 $\mu$m, the weight, correspondingly, may be from 15 to 350 g/m$^2$, preferably from 15 to 100 g/m$^2$, the maximum tensile strength in the lengthwise direction may be from about 5 to 100 N/cm, preferably from 2 to 40 N/cm, and the elongation at break in the lengthwise direction may be from 100 to 1000%.

The backing material, which plays a supporting role for the film, remains on the dressing when the dressing is applied and is only removed subsequently, preferably comprises a polyethylene film of approximately 80 $\mu$m in thickness which on its film-facing side is slightly roughened and is therefore matte but still has a transluscent effect. It is also possible to use other films comprising, for example, polypropylene, polyester, PVC or suitable thin, coated paper, provided only that they are sufficiently pliant so as not to cause disruption when the dressing is applied.

The adhesion of the film to the backing material should be between 0.01 and 0.5 N/cm and should thus be much lower than the adhesion of the adhesive layer on the skin after the dressing material is applied.

The technical data of the film may be situated within the following ranges:

| | |
|---|---|
| Thickness | from 30 to 300 $\mu$m |
| Weight | from 30 to 350 g/m$^2$ |
| Maximum tensile strength, lengthwise | from 5 to 100 N/cm |
| Elongation at break, lengthwise | from 10 to 1000% |

Its surface to the film may be smooth, roughened or slightly embossed.

In another preferred embodiment of the dressing material, there is at least one grip strip on the backing material.

The grip strips may be disposed within the peripheral boundary of the backing material. In other words, the grip strip, of which there is preferably only one and which is mounted at any desired point on the backing material, does not protrude beyond the edge of the said material and is thus not lost if smaller plasters in all possible shapes are punched from the prefabricated material. Preferably, the grip strip extends over the entire length or width of the plaster, depending on the plaster shape. Advantageously, the grip strip is fastened on the backing material by being stuck on in a narrow edge region and having on one side, to the left or right thereof, a free, unbonded engagement area of at least approximately 5 mm. The grip strip may cover the entire plaster, especially if the plaster is very small; alternatively, it may cover it only partly. In one of the possible and preferred embodiments, the strip ends flush with one side edge. In another embodiment, the grip strip is fixed on the backing material in a narrow central stripe-shaped region and has on both sides thereof a free engagement region of at least approximately 5 mm in width.

Furthermore, separate grip strips may be firmly attached along two opposing edges of the backing material, such that the grip strips are connected to the backing material by only part of their width and with the other, preferably larger part of their width protrude beyond the dressing material.

Depending on the material and on the processing machinery, the attachment of the grip strips on the backing material may be realized in a variety of ways, preferably by adhesive bonding or welding. Adhesive bond is realized, for example, by inserting a strip of a double-sided adhesive tape between the backing material and the grip-strip stripe in the region to be bonded, or by means of a coating of a hot-melt or a self-adhesive composition applied from solution or dispersion.

The inventive concept then also embraces a process for producing a dressing material of the invention, in which
- the film is produced in at least one layer on the backing material by flow coating, knife coating or extrusion,
- the film is printed on the side facing away from the backing material,
- if desired, a further film is applied to the print of the film by flow coating, knife coating or extrusion, a self-adhesive coating is applied to the film or to the further film.

The dressing material of the invention is then generally sealed individually into an appropriately shaped envelope and, if appropriate, is sterilized by means of gamma rays.

For use, the plaster is removed from the envelope, the protective lining over the adhesive layer is removed, the plaster is stuck onto the wound and then the readily redetachable backing material on the reverse side of the film is peeled off without residue using the grip strip.

The handling of the dressing requires no use instructions, since the mode of use is virtually self-evident. Since, moreover, the entire dressing including the supporting backing film is transparent, it may be precisely applied without difficulty.

BRIEF DESCRIPTION OF THE DRAWINGS

FIG. 1 shows by way of example the dressing material of the invention, with the layer thicknesses enlarged. In the figure, (1) denotes the backing layer, preferably of polyethylene, (2) denotes the first film, preferably of polyurethane, it being possible for this layer itself to comprise a plurality of individual plies, (3) denotes the ply of the impression, (4) denotes the second film, preferably of polyurethane, it being possible for this layer likewise to itself comprise a plurality of individual plies, (5) denotes the self-adhesive layer, (6) and (7) denote the protective linings for the self-adhesive layer, (8) denotes the grip strip formed onto the film, and (9) denotes the adhesive layer for attaching the grip strip on the backing.

In the text below, using a number of examples, particularly advantageous embodiments of the dressing material will be depicted, without wishing to restrict the invention unnecessarily as a result.

EXAMPLE 1

The dressing material of the invention comprises an anionic aliphatic polyester polyurethane dispersion film (Impranil® DLN dispersion from Bayer) measuring 50×50 mm. The film has a thickness of 0.1 mm.

The film is coated on one side with a dermatologically compatible adhesive layer based on crosslinked polyacrylic acid derivatives.

EXAMPLE 2

The dressing material of the invention is formed, in the same way as in Example 1, by a polyurethane gel "Cutinova thin"® from Beiersdorf AG, which is additionally enclosed with the polyester polyurethane dispersion film (Impranil® DLN dispersion from Bayer) from example 1.

What is claimed is:

1. Film-based dressing material which have the properties of:
   (a) a thickness of 30 to 300 $\mu$m;
   (b) a weight of 30 to 350 g/m$^2$;
   (c) a maximum lengthwise tensile strength of 5 to 100 N/cm; and
   (d) a lengthwise elongation at break of 10 to 1000%;
   wherein said film-based dressing material is lined on the side remote from the wound with a transparent backing material of the same size as the film, wherein the wound-facing side of the film bears an imprint and is covered by at least one further film.

2. Dressing material according to claim 1, wherein the wound-facing side of the dressing material is provided with a self-adhesive layer, optionally on which a wound pad smaller than the adhesive area is disposed.

3. Dressing material according to claim 1, wherein the film comprises polyurethane.

4. Dressing material according to claim 1, wherein there is at least one grip strip on the backing material.

5. The film-based dressing material of claim 1, which have the properties of:
   (a) a thickness of 15 to 80 $\mu$m;
   (b) a weight of 15 to 100 g/m$^2$;
   (c) a maximum lengthwise tensile strength of 2 to 40 N/cm; and
   (d) a lengthwise elongation at break of 100 to 1000%.

6. The film-based dressing material of claim 1 wherein the imprint is applied by reversal printing.

7. The film-based dressing material of claim 1 wherein the backing material is a polyethylene film.

8. Process for producing a dressing material according to claim 1, wherein
   a) a film is produced in at least one layer on a backing material by flow coating, knife coating or extrusion,
   b) the film is printed on the side facing away from the backing material,
   c) a further film is applied to the print of the film by flow coating, knife coating or extrusion,
   d) a self-adhesive coating is applied to the film or to the further film.

* * * * *